US008553970B2

(12) United States Patent
Auerbach

(10) Patent No.: US 8,553,970 B2
(45) Date of Patent: Oct. 8, 2013

(54) SYSTEM AND METHOD FOR GENERATING SPATIAL SIGNATURES

(75) Inventor: Ditza Auerbach, Aseret (IL)

(73) Assignee: Applied Materials Israel, Ltd., Rehovot (IL)

(*) Notice: Subject to any disclaimer, the term of this patent is extended or adjusted under 35 U.S.C. 154(b) by 0 days.

(21) Appl. No.: 13/585,730

(22) Filed: Aug. 14, 2012

(65) Prior Publication Data
US 2013/0051653 A1   Feb. 28, 2013

Related U.S. Application Data

(63) Continuation of application No. 12/477,061, filed on Jun. 2, 2009, now Pat. No. 8,254,661.

(60) Provisional application No. 61/058,129, filed on Jun. 2, 2008.

(51) Int. Cl.
G06K 9/00 (2006.01)
(52) U.S. Cl.
USPC .............. 382/141; 382/145; 382/150; 702/81
(58) Field of Classification Search
USPC ...................... 382/141–153; 716/52, 112; 356/237.1–237.5; 702/81–84, 35
See application file for complete search history.

(56) References Cited

U.S. PATENT DOCUMENTS

| 5,982,920 | A  | * | 11/1999 | Tobin et al. ................... 382/145 |
| 5,991,699 | A  |   | 11/1999 | Kulkarni et al. |
| 6,718,526 | B1 |   | 4/2004  | Eldredge |
| 6,841,403 | B2 |   | 1/2005  | Tanaka et al. |
| 7,084,968 | B2 | * | 8/2006  | Shibuya et al. ............. 356/237.2 |
| 7,359,544 | B2 |   | 4/2008  | Gao |
| 7,676,077 | B2 |   | 3/2010  | Kulkarni et al. |
| 7,738,093 | B2 | * | 6/2010  | Alles et al. .................. 356/237.5 |
| 8,213,704 | B2 | * | 7/2012  | Peterson et al. ............. 382/145 |
| 8,254,661 | B2 | * | 8/2012  | Auerbach ..................... 382/141 |
| 2003/0130806 | A1 |   | 7/2003  | Mizuno et al. |
| 2007/0230770 | A1 |   | 10/2007 | Kulkarni et al. |
| 2009/0105990 | A1 |   | 4/2009  | Shibuya et al. |
| 2009/0297019 | A1 |   | 12/2009 | Zafar et al. |
| 2010/0119144 | A1 |   | 5/2010  | Kulkarni et al. |
| 2011/0286656 | A1 | * | 11/2011 | Kulkarni et al. ............. 382/144 |

OTHER PUBLICATIONS

Non-Final Office Action of Sep. 29, 2011 for U.S. Appl. No. 12/477,061; 8 pages.
Final Office Action of Feb. 15, 2012 for U.S. Appl. No. 12/477,061; 11 pages.
Notice of Allowance of Apr. 26, 2012 for U.S. Appl. No. 12/477,061; 8 pages.

* cited by examiner

*Primary Examiner* — Hoa Pham
(74) *Attorney, Agent, or Firm* — Kilpatrick Townsend & Stockton LLP

(57) ABSTRACT

A system and method for performing spatial signature analysis, the system including a memory unit for storing wafer defect density maps of multiple resolutions, derived from a defect map obtained by an inspection tool; an analyzer for analyzing the wafer defect density maps to identify zones of interest; and a spatial signature generator for generating spatial signatures in response to relations between zones of interest of different density resolution.

17 Claims, 14 Drawing Sheets

Portion 20

Portion 30

Density color scale

```
┌─────────────────────────────────────────────────────────────────────┐
│ Analyzing wafer defect density maps of multiple resolutions to       │
│ identify zones of interest. 910                                      │
└─────────────────────────────────────────────────────────────────────┘
                                    │
┌─────────────────────────────────────────────────────────────────────┐
│ Limiting a defect density distribution within each spatial signature. 931 │
├─────────────────────────────────────────────────────────────────────┤
│ Generating a spatial signature that includes a set of zones of interest of different defect densities, │
│ wherein at least two zones of interest of the set are partially overlapping. 932 │
├─────────────────────────────────────────────────────────────────────┤
│ generating a spatial signature that comprises a set of zones of interest; wherein the set comprises a peak │
│ zone of interest and at least one other zone of interest; wherein at least two different zones of interest of │
│ the set have different defect densities and a defect density of the peak zone of interest is higher than │
│ defect density of each of the at least one other zone of interest, wherein the peak zone of interest is │
│ included within another zone of interest of the set. 933 │
├─────────────────────────────────────────────────────────────────────┤
│ Limiting a defect density distribution of zones of interest of a set of zones of interest. 934 │
├─────────────────────────────────────────────────────────────────────┤
│ Generating a spatial signature that includes multiple sets of zones of interests. 935 │
├─────────────────────────────────────────────────────────────────────┤
│ Limiting a defect intensity distribution within multiple sets of zones of interest. 936 │
├─────────────────────────────────────────────────────────────────────┤
│ Generating a spatial signature that comprises multiple sets of zones of interest wherein each set │
│ comprises zones of interest of at least a minimal number of defect densities. 937 │
├─────────────────────────────────────────────────────────────────────┤
│ Representing zones of interest of by a tree and processing the tree to determine spatial signatures. 938 │
├─────────────────────────────────────────────────────────────────────┤
│ Filtering (ignoring) sparse spatial signatures. A sparse spatial signature is a spatial signature that │
│ includes zones of interest of a resolution that is below a predefined resolution threshold. 939 │
├─────────────────────────────────────────────────────────────────────┤
│ Clustering spatial signatures that resemble each other. 940 │
├─────────────────────────────────────────────────────────────────────┤
│ Identifying seeds of signatures as zones of interest of higher defect density than adjacent zones of │
│ interest and subsequently coalescing the seeds to include additional regions of interest. 941 │
├─────────────────────────────────────────────────────────────────────┤
│ Finding repetitive spatial signatures. 942 │
├─────────────────────────────────────────────────────────────────────┤
│ Generating a spatial signature map that represents the locations of spatial signatures, wherein similar │
│ spatial signatures are assigned the same signature identifier. This spatial signature map can be displayed │
│ to a user during stage 950. 943 │
├─────────────────────────────────────────────────────────────────────┤
│ Associating multiple attributes to each spatial signature. These attributes can include the number of │
│ defects, the shape of the spatial signature, the highest defect density level, the lowest defect density │
│ level, zones of interest or areas of interest included in the spatial signature, defects included in the │
│ spatial signature, and the like. 944 │
├─────────────────────────────────────────────────────────────────────┤
│ Outlier removal. 945 │
└─────────────────────────────────────────────────────────────────────┘
│ Generating spatial signatures in response to locations of zones of interest and │
│ density of defects within the zones of interest. 930 │
                                    │
┌─────────────────────────────────────────────────────────────────────┐
│ Outputting information indicative of a plurality of spatial signatures. 951 │
├─────────────────────────────────────────────────────────────────────┤
│ Storing information indicative of a plurality of spatial signatures. 952 │
├─────────────────────────────────────────────────────────────────────┤
│ Transmitting information indicative of a plurality of spatial signatures. 953 │
├─────────────────────────────────────────────────────────────────────┤
│ Displaying information indicative of a plurality of spatial signatures. 954 │
├─────────────────────────────────────────────────────────────────────┤
│ Defining review sites for a review tool in response to detected spatial signatures. │
│ The review sites can be diversified between different spatial signatures. 955 │
├─────────────────────────────────────────────────────────────────────┤
│ Triggering a review tool based classification of defects in response to detected │
│ spatial signatures. 956 │
└─────────────────────────────────────────────────────────────────────┘
│ Responding to the spatial signatures. 950 │

900                        FIG. 9
``` ical description when read
SYSTEM AND METHOD FOR GENERATING SPATIAL SIGNATURES

REFERENCE TO RELATED APPLICATIONS

This application is a CONTINUATION of, claims the priority to and incorporates by reference U.S. application Ser. No. 12/477,061 filed Jun. 2, 2009, now U.S. Pat. No. 8,254,661 which claims the priority benefit of U.S. Provisional Patent Application No. 61/058,129, filed Jun. 2, 2008.

FIELD OF THE INVENTION

This invention is generally in the field of spatial signature analysis and especially for evaluating wafers using a spatial signature analysis.

BACKGROUND OF THE INVENTION

Wafers are manufactured by a very complex manufacturing process. Various inspection tools and review tools have been developed in order to detect defects and classify defects that occur during the manufacturing process.

A wafer evaluation process usually includes inspecting the wafer with an inspection tool to detect suspected defects, extracting defects of interest out of the suspected defects and classifying the defects.

The wafer evaluation process should be tailored in order to satisfy seemingly contradicting requirements such as high reliability, repeatability, low rate of mistakes, high throughput, high resolution, vast amount of information, limited processing and storage resources, and the like. In addition, despite the large number of suspected defects that can be found by an inspection tool only a small portion of these suspected defects are processed further by other tools or by operators.

The outcome of this tailoring process is known as a recipe. A recipe includes the optimal methods and processes that should be applied during the evaluation process.

The following publications relate to spatial signature analysis: U.S. Pat. Nos. 6,718,526; 7,359,544; 6,841,403; and 5,991,699.

There is a growing need to provide a method and system for improving the spatial signature analysis of inspection defect maps. There is further a need to provide a method and system for assisting in optimizing a recipe in terms of both duration and performance.

SUMMARY OF THE INVENTION

According to an embodiment of the invention, there is provided a method for spatial signature analysis, the method includes: analyzing wafer defect density maps of multiple resolutions to identify zones of interest; wherein the wafer defect density maps are derived from a defect map obtained by an inspection tool; and generating spatial signatures in response to relations between zones of interest of different density resolution.

According to another embodiment of the invention, there is provided a system for spatial signature analysis, the system includes: a memory unit for storing wafer defect density maps of multiple resolutions; an analyzer for analyzing the wafer defect density maps to identify zones of interest; and a spatial signature generator for generating spatial signatures in response to relations between zones of interest and density of defects within the zones of interest.

According to yet another embodiment of the invention, there is provided a method for operating an inspection tool, the method comprises: for at least one defect map of a substrate produced by the inspection tool, generating two or more substrate defect density maps of multiple resolutions to identify zones of interest; generating spatial signatures in response to relations between zones of interest and density of defects within the zones of interest; and based on said spatial signatures, adjusting one or more inspection condition of the inspection tool, if required. According to an embodiment of the invention, the inspection condition is adjusted in response to analysis of spatial signatures corresponding to a single defect map. According to another embodiment of the invention, the inspection condition is adjusted in response to analysis of spatial signatures corresponding to more than one defect map, each defect map produced by utilizing different inspection conditions.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 9 is a flow chart of a method, according to an embodiment of the invention.

Figure 1A:
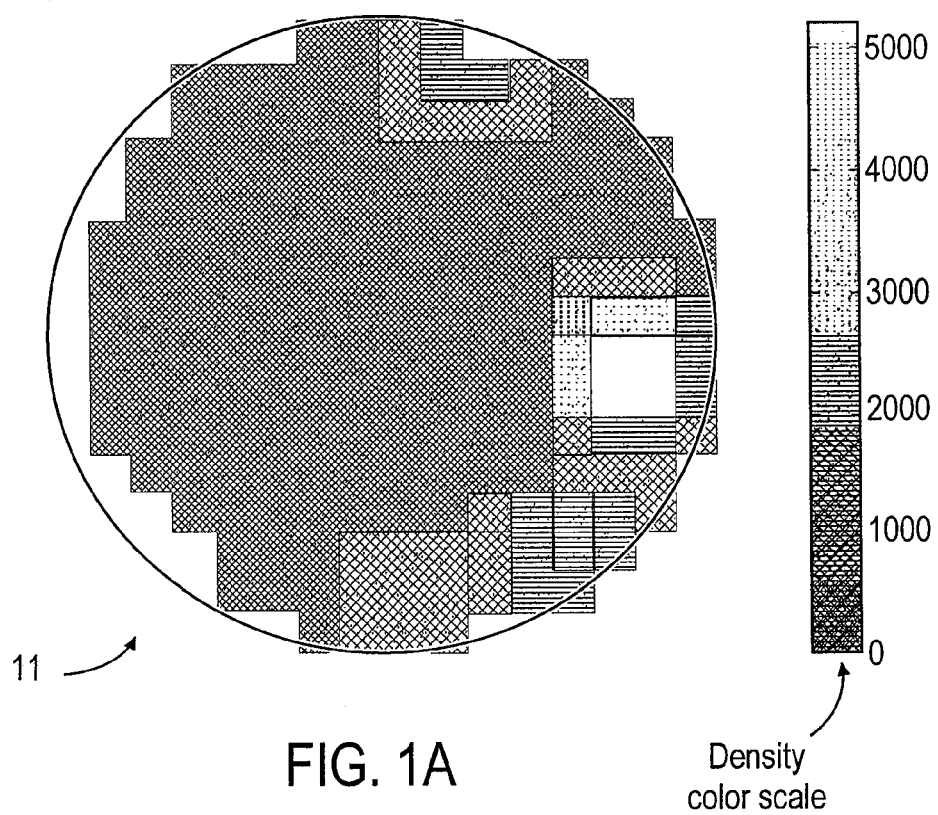
FIGS. 1A-1E illustrate wafer defect density maps of different resolutions, according to an embodiment of the invention.
Figure 1B:
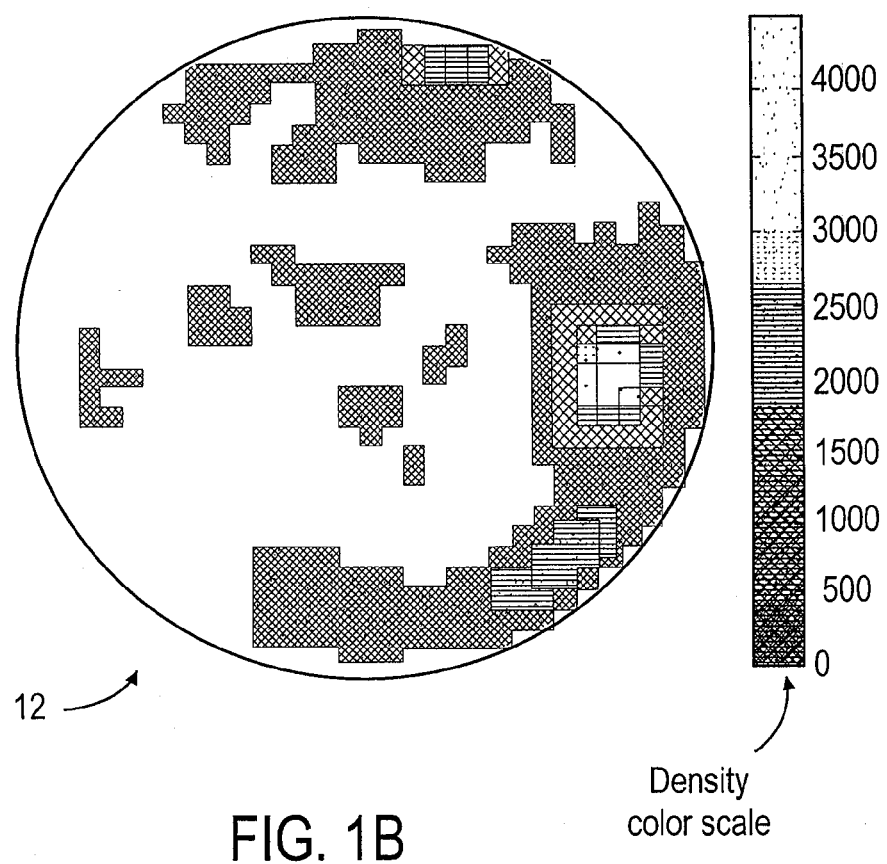
Figure 1C:
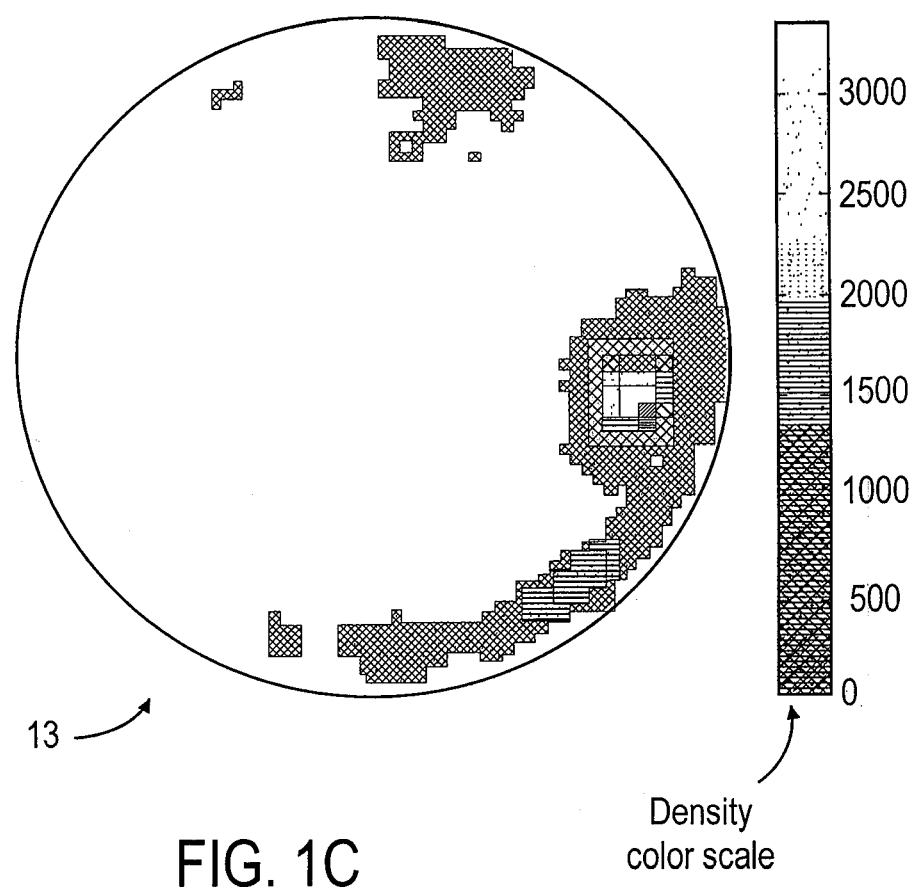
Figure 1D:
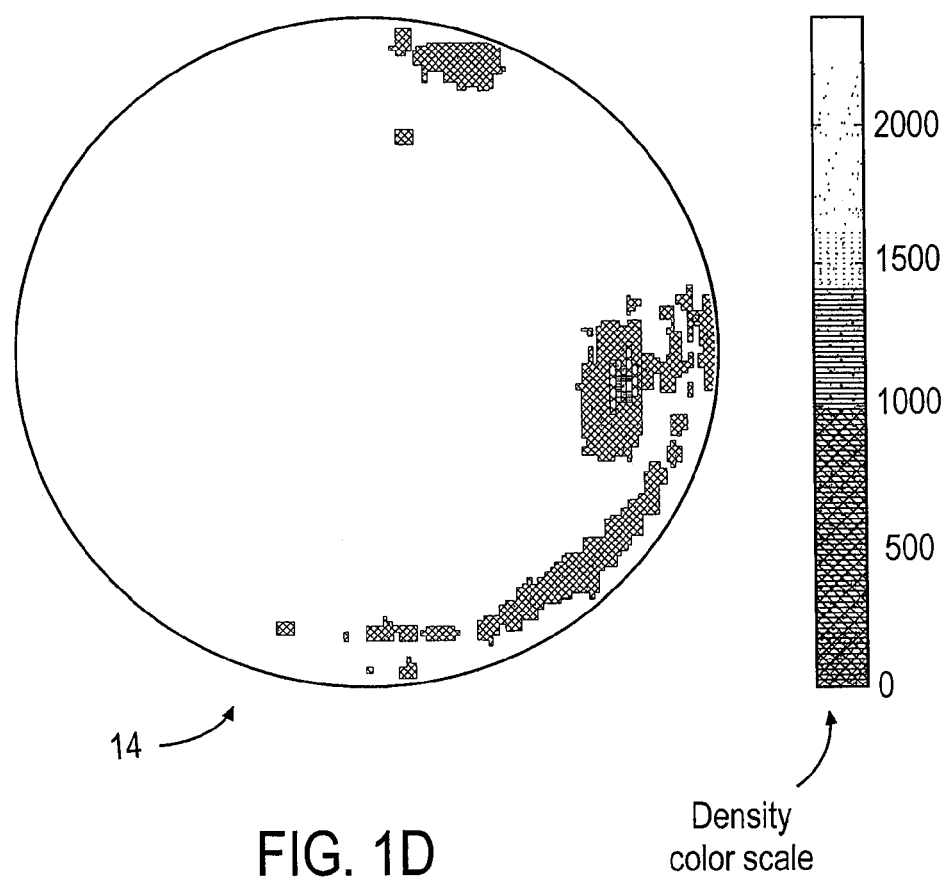
Figure 1E:
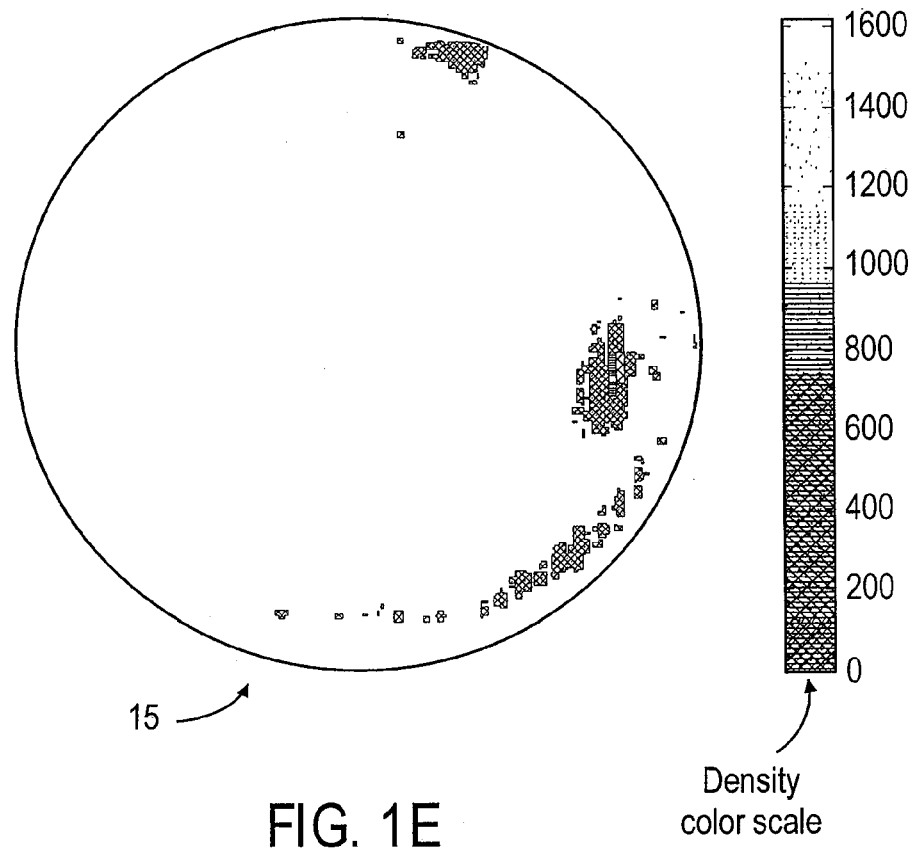

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Methods and system for spatial signature analysis are provided. The spatial signatures can be used to optimize an inspection recipe, define review sites, filter images obtained during an inspection process, and the like. The spatial signatures are obtained from multiple wafer defect density maps of different resolutions that provide indication about different defect density levels.

FIGS. 1A-1E illustrate wafer defect density maps 11-15 of different resolutions, respectively, according to an embodiment of the invention.

Each wafer defect density map includes information about multiple areas of the wafer. The wafer defect density map provides an indication about a defect density (number) of each area (represented by a density color scale). Maps of different resolution provide information about different defect density levels.

A wafer defect density map is generated by thresholding defect densities. It is noted that according to another embodiment of the invention wafer defect density maps of different resolutions differ from each other by their thresholds. For example, one wafer defect density map can indicate which areas of the wafer include a defect density that is above a first defect density threshold and another wafer defect density map can indicate which areas of the wafer include a defect density that is above a second defect density threshold that differs from the first defect density threshold.

Because a defect density of an area is proportional to a ratio between the number of defects and the size of the area, then wafer defect density maps of different resolution can be characterized by different area sizes, and additionally or alternatively, by different number of defects per area.

According to one embodiment of the invention wafer defect density maps of different resolutions differ from each other by the size of areas of which their density is expressed in these wafer defect density maps. For example, a higher resolution wafer defect density map provides an indication about the defect density within smaller areas in comparison to those of a lower resolution wafer defect density map, as illustrated in FIGS. 1A-1E. The areas of wafer defect density map 11 are larger than those of wafer defect density map 15, although all wafer defect density maps can be obtained by processing images of the wafer that were obtained at the same digital resolution.

According to an embodiment of the invention the defect density threshold equals a predefined number of defects per area. Each wafer defect density map will indicate areas that include more than the predefined number of defects. By defining areas of different sizes for different map defect maps this predefined number represents defect densities.

The ratio between defect density thresholds of different wafer defect density maps can be constant but this is not necessarily so. For example, if the defect density threshold of wafer defect density maps 11-15 are denoted DT1-DT5 then a fixed ratio means that (DT2/DT1)=(DT3/DT2)=(DT4/DT3)=(DT5/DT4). A varying ratio between the defect density threshold means that the mentioned above ratios between DT1-DT5 can differ from each other, thus for example (DT2/DT1) can differ from (DT3/DT4) and from (DT5/DT4).

Figure 2:
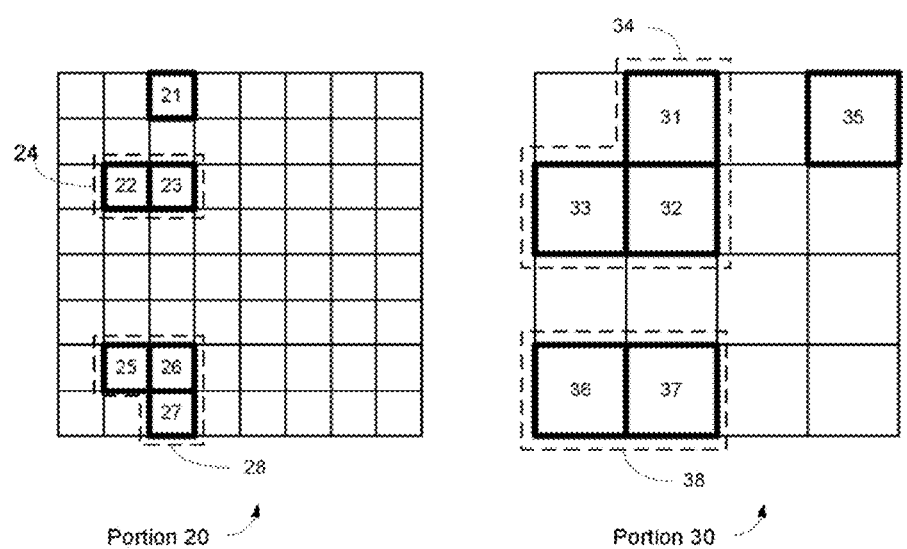
FIG. 2 illustrates two portions of wafer defect density maps of different resolutions, according to an embodiment of the invention.

FIG. 2 illustrates two portions 20 and 30 of wafer defect density maps of different resolutions, according to an embodiment of the invention. These portions relate to the same locations on the wafer.

Portions 20 and 30 belong to different wafer defect density maps of different resolutions. The resolution of the wafer defect density map that includes portion 20 is twice higher than the resolution of the wafer defect density map that includes portion 30. This is illustrated by the 1:4 ratio between the size of areas included in portions 20 and 30. Portions 20 and 30 provide an indication of which areas include more than a predefined number (denoted D) of defects.

Portion 20 includes six areas 21, 22, 23, 25, 26 and 27, each area including more than D defects. Portion 30 includes six areas 31, 32, 33, 35, 36 and 37, each area including more than D defects. Because of the 4:1 ratio between the sizes of the areas of the different portions, areas 21, 22, 23, 25, 26 and 27 are associated with a defect density level that may be up to four times higher than the defect density level associated with areas 31, 32, 33, 35, 36 and 37.

Areas 21, 22, 23, 25, 26, 27, 31, 32, 33, 35, 36 and 37 can be regarded as areas of interest as they are indicative of defect densities that correspond to the resolution of their respective wafer defect density maps.

According to an embodiment of the invention adjacent areas of interest (of the same density map, same density resolution) are clustered to provide zones of interest. According to an embodiment of the invention, a zone of interest represents an area containing defects with a density above a predetermined density threshold. Portion 20 includes three zones of interest: 21, 24 and 28. Zone of interest 21 includes area of interest 21. Zone of interest 24 includes areas of interest 22 and 23. Zone of interest 28 includes areas of interest 25, 26 and 27. Portion 30 includes three zones of interest: 34, 35 and 38. Zone of interest 34 includes areas of interest 31, 32 and 33. Zone of interest 35 includes area of interest 35. Zone of interest 38 includes areas of interest 36 and 37.

As a result of the thresholding zones of interest 21 and 24 are included within zone of interest 34 while zone of interest 28 is included within zone of interest 38. Zone of interest 35 of portion 30 does not include any zone of interest of portion 20 because it is less dense.

A location of the wafer can be associated with multiple zones of interest of different defect density levels. The zone of interest of highest defect density associated with this location is a peak zone of interest. When viewing wafer defect density maps of different resolution a peak zone of interest is the first zone of interest to appear at a certain location of a higher resolution wafer defect density map. In other words, if the different wafer defect density maps are virtually placed over each other—having the lower resolution wafer defect density map at the bottom—then the highest zones of interest per each location are the peak zones of interest—they represent "local" peaks of defect density distributions.

Referring to the example set forth in FIG. 2, and assuming that portion 20 belongs to the highest resolution wafer defect density map then zone of interest 35 of portion 30 is a peak zone of interest because it is associated with locations of the wafer that are not associated with zones of interest that belong to portion 20. Zones of interest 21, 24 and 28 are peak zones of interest because portion 20 belongs to the highest resolution wafer defect density map.

The process of spatial signature generation includes detecting zones of interest and generating spatial signatures. This can include ignoring zones of interest, grouping zones of interest and the like.

Defect densities can dramatically vary across the wafer. The ratio between defect densities of different areas can exceed 10,000. Various prior art methods used to find spatial signatures that were spatially separated from each other but should be responsive to a very wide range of defect densities. The suggested method and system allow a spatial overlap between spatial signatures but simplifies the analysis of defects by limiting the defect density variation within each spatial signature. A single spatial signature can include a certain range of defect density levels. This certain range can include, for example, a certain number of wafer defect density maps that can contribute to a certain spatial signature, a minimal number of resolution levels included in each spatial signature and the like.

The generation of spatial signatures can be illustrated by graphs that represent the relationships between different zones of interest. The tree includes multiple nodes. Nodes are arranged in different levels that represent different resolution levels. Nodes of the tree that are connected to each other represent zones of interest of consecutive resolution wafer defect density maps which overlap.

It is noted that the graph representation can be replaced by another equivalent representation and that the reference to such a graph representation is brought for sake of clarity.

For simplicity of explanation zones of interest of different wafer defect density maps that are associated with the same location are regarded as partially overlapping zones of interest. Referring to the example set forth in FIG. 2, zone of interest 34 partially overlaps zones of interest 21 and 24.

Figure 3:
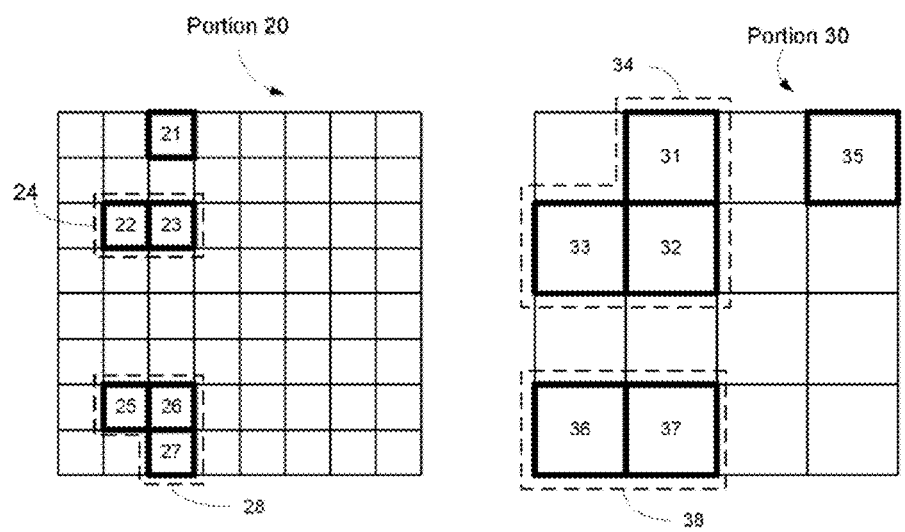
FIG. 3 illustrates a tree representation of the zones of interest of the two portions of FIG. 2, according to an embodiment of the invention.

FIG. 3 illustrates a tree representation of the zones of interest of portions 20 and 30, according to an embodiment of the invention.

The leaf nodes of the tree represent zones of interest of the highest resolution wafer defect density map as well as peak zones of interest that do not belong to the highest resolution wafer defect density map. The root node of a tree (not shown in FIG. 3) illustrates one or more zones of interest of the lowest resolution.

Linked nodes of the tree represent zones of interest that partially overlap. A sequence of linked nodes can include intermediate nodes that show zones of interest that differ from the peak zones of interest but are not the lower resolution zones of interest. Nodes that represent partially overlapping zones of interest are linked to each other. A zone of interest that is associated with a parent node includes a zone of interest that is represented by an ancestor node.

Assuming that portion 20 belongs to the highest resolution map then FIG. 3 illustrates leaf nodes that correspond to zones of interest of portion 20 as well as other nodes.

Peak zones of interest 28, 24 and 21 of portion 20 are represented by leaf nodes 41, 42 and 43 respectively.

Peak zone of interest 35 of portion 35 is represented by leaf node 53.

The tree also includes intermediate nodes 51 and 52 that represent zones of interest 38 and 34 respectively.

Node 51 is connected to node 41 as these nodes represent partially overlapping zones of interest. Node 52 is connected to nodes 42 and 43 as the latter nodes represent zones of interest that are included in zone of interest 34. Node 53 is not connected to any leaf node as it represents a peak zone of interest (35) that does not partially overlap with any zone of interest of portion 20.

The number of partially overlapping zones of interest can exceed two, especially if more than two resolutions are defined.

Figure 4:
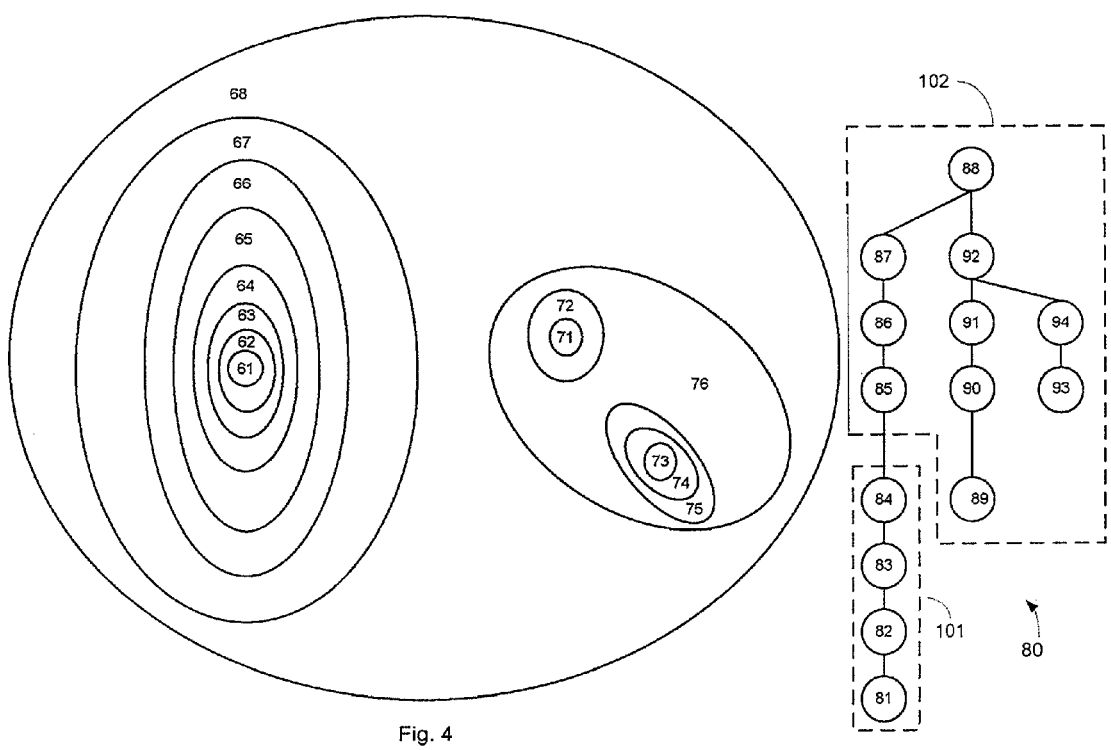
FIG. 4 illustrates two spatial signatures and their tree, according to an embodiment of the invention.

FIG. 4 illustrates three sets of zones of interest and tree 80 that represents these sets of zones of interest, according to an embodiment of the invention.

Figure 5:
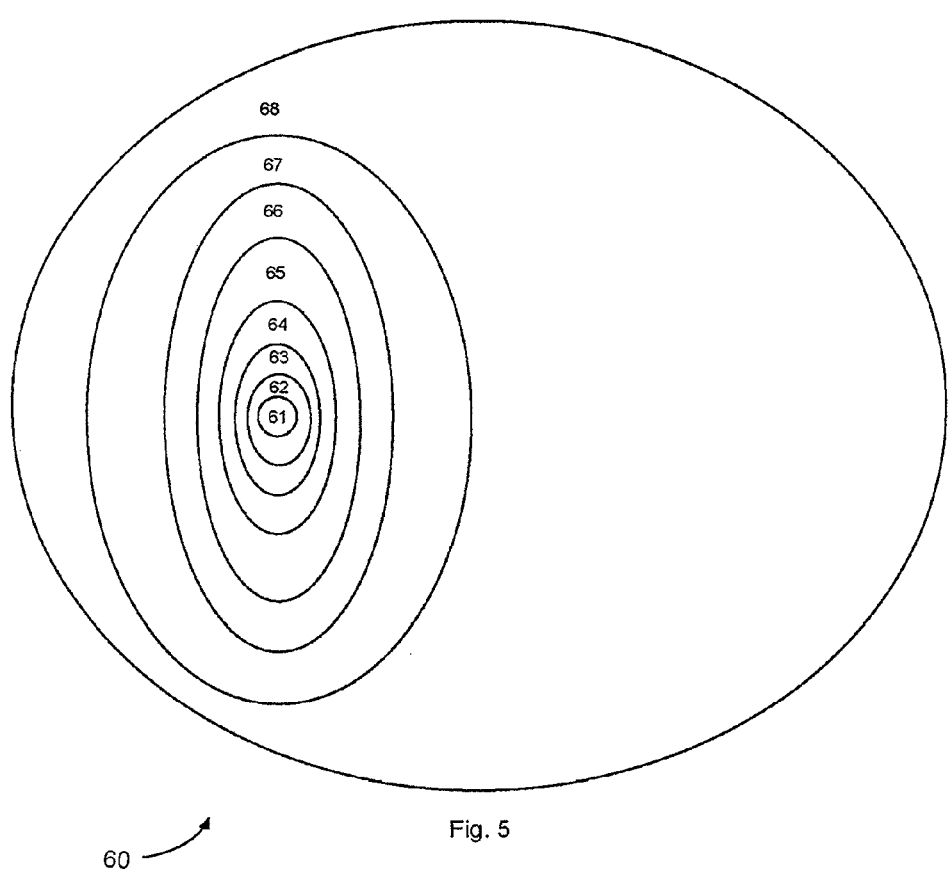
FIG. 5 illustrates a set of zones of interest according to an embodiment of the invention.

A first set (denoted 60 in FIG. 5) includes zones of interest 61, 62, 63, 64, 65, 67 and 68 that are associated with eight different resolutions, one of interest 61 being a peak zone of interest of first set 60.

Each zone of interest of a certain resolution is included within all zones of interest of lower resolution. For example, zone of interest 61 is included in each of zones of interest 62-68.

Figure 6:
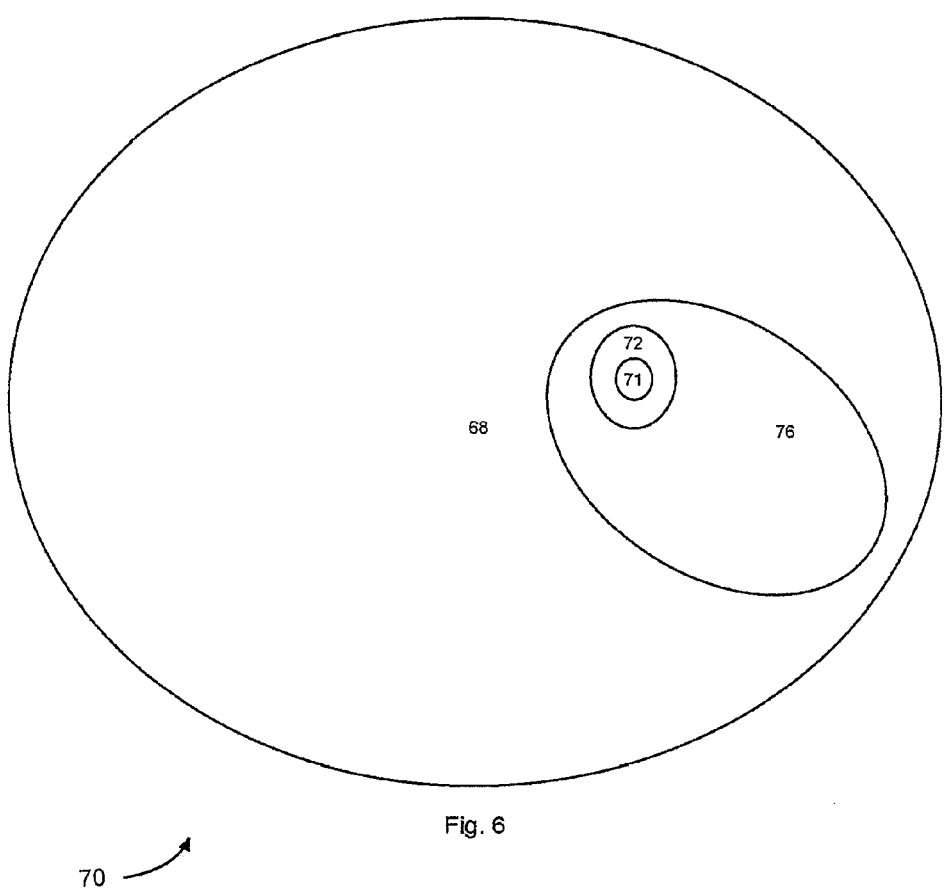
FIG. 6 illustrates a set of zones of interest according to an embodiment of the invention.

A second set (denoted 70 in FIG. 6) includes zones of interest 71, 72, 76 and 68 that are associated with four different resolutions, zone of interest 71 being a peak zone of interest of second set 70.

Figure 7:
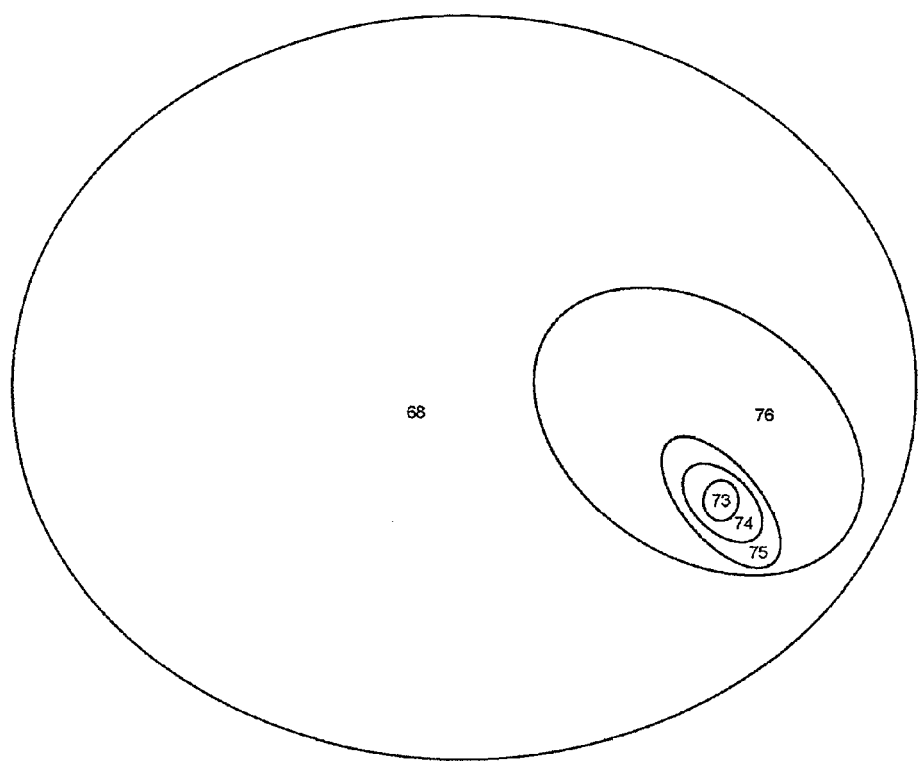
FIG. 7 illustrates a set of zones of interest according to an embodiment of the invention.

A third set (denoted 79 in FIG. 7) includes zones of interest 73, 74, 75, 76 and 68 that are associated with five different resolutions, zone of interest 73 being a peak zone of interest of third set 79.

All three sets share a common (lowest resolution) zone of interest, zone of interest 68. Accordingly, zone of interest 68 is represented by root node 88.

Zones of interest 61-68 of first set 60 are represented by a sequence of nodes 81-88 that are linked to each other. Zones of interest 71, 72, 76 and 68 of second set 70 are represented by a sequence of nodes 93, 94, 92 and 88 that are linked to each other. Zones of interest 73, 74, 75, 76 and 68 are represented by a sequence of nodes 89, 90, 91, 92 and 88 that are linked to each other. Nodes (such as nodes 92 and 88) that are shared between sequences represent zones of interest that belong to multiple sets.

As indicated above, a spatial signature can include a limited number of resolutions. FIG. 4 illustrates a spatial signature generation rule that requires that at least four different resolutions are included in each spatial signature.

The search for spatial signatures starts from a leaf of the tree, and a minimum of four nodes (of four different resolutions) should be included in each spatial signature.

The search for the first spatial signature starts at leaf node 81. The first spatial signature (denoted 101) includes a sequence of nodes 81, 82, 83 and 84.

The search for the second spatial signature starts from either one of leaf nodes 89 or 93.

When a minimal number of resolutions is required for each sequence of the node, it can be shown that although sequence of nodes 89, 90, 91 and 92 includes four resolutions it can not define a spatial signature as node 92 also belongs to another sequence that includes only two additional nodes 93 and 94.

Accordingly in order for each sequence to include at least four different nodes, the second spatial signature should include nodes 85, 86, 87, 88, 89, 90, 91, 92, 93 and 94. This spatial signature is denoted 102.

Figure 8:
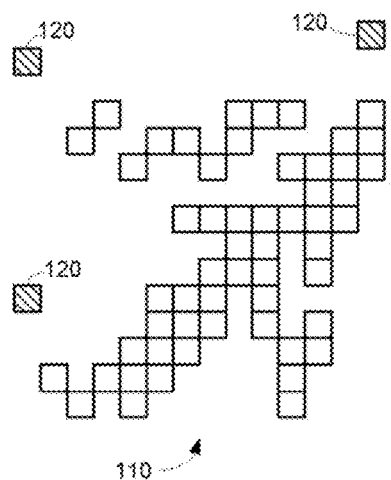
FIG. 8 illustrates a removal of outlier defects from a spatial signature, according to an embodiment of the invention.

A spatial signature can include zones of interest of different sizes. These larger areas can be partitioned to smaller sub-areas in order to delete smaller areas that do not include dense defects. This is illustrated in FIG. 8 that shows that sparse defects 120 are removed from spatial signature 110.

FIG. 9 illustrates method 900 for spatial signature analysis, according to an embodiment of the invention.

Method 900 can include stage 910 of analyzing wafer defect density maps of multiple resolutions to identify zones of interest. Stage 910 can be preceded by generating or receiving a map of suspected defects and processing it to provide wafer density maps of multiple resolutions.

Stage 910 is followed by stage 930 of generating spatial signatures in response to relations between zones of interest and density of defects within the zones of interest.

Stage 930 can include one or more of stages 931-945. FIG. 9 illustrates these stages (various relations between zones of interest and density of defects within the zones of interest) according to an embodiment of the invention.

Stage 931 includes limiting a defect density variation within each spatial signature. This can include limiting the difference between a highest defect density and a lowest defect density per spatial signature. This limitation can be a maximal ratio between these defect density levels.

Stage 932 includes generating a spatial signature that includes a set of zones of interest of different defect densities, wherein at least two zones of interest of the set are partially overlapping.

Stage 933 includes generating a spatial signature that comprises a set of zones of interest; wherein the set comprises a peak zone of interest and at least one other zone of interest; wherein at least two different zones of interest of the set have different defect densities and a defect density of the peak zone of interest is higher than defect density of each of the at least one other zone of interest; and wherein the peak zone of interest is included within another zone of interest of the set.

Stage 934 includes limiting a defect density variation of zones of interest of a set of zones of interest.

Stage 935 includes generating a spatial signature that includes multiple sets of zones of interests.

Stage 936 includes limiting a defect intensity variation within multiple sets of zones of interest.

Stage 937 includes generating a spatial signature that comprises multiple sets of zones of interest wherein each set comprises zones of interest of at least a minimal number of defect densities.

Stage 938 includes representing zones of interest by a tree and processing the tree to determine spatial signatures.

Stage 939 includes filtering (ignoring) sparse spatial signatures. A sparse spatial signature is a spatial signature that includes zones of interest of a resolution below a predefined resolution threshold. Additionally or alternatively, a sparse spatial signature can include zones of interest with respective defect densities is not substantially above that of sparse areas of defects.

Stage 940 includes clustering spatial signatures that resemble each other. This stage can reduce the number of spatial signature types that are displayed to a user. The clustering will include assigning the same spatial signature identifier to similar spatial signatures.

Stage 941 includes identifying seeds of signatures as zones of interest of higher defect density than adjacent zones of interest and subsequently coalescing the seeds to include additional regions of interest.

Stage 942 includes finding repetitive spatial signatures.

Stage 943 includes generating a spatial signature map that represents the locations of spatial signatures, wherein similar spatial signatures are assigned the same signature identifier. This spatial signature map can be displayed to a user during stage 950.

Stage 944 includes associating multiple attributes to each spatial signature. These attributes can include the number of defects, the shape of the spatial signature, the highest defect density level, the lowest defect density level, zones of interest or areas of interest included in the spatial signature, defects included in the spatial signature, and the like.

Stage 945 includes outlier removal. A spatial signature shape is defined by the lower resolution zones of interest included in the spatial signature. These lower resolution zones of interest can be partitioned to smaller areas that are analyzed, one smaller area after the other, in order to remove smaller areas that are not dense enough or remove defects that are surrounded by sparse areas. For example, these areas can be of the same size as the areas of the highest resolution wafer defect density map, but this is not necessarily so. FIG. 8 illustrates a removal of defects 120 that are surrounded by sparse areas and are located near the perimeter of spatial signature 110.

Stage 930 is followed by stage 950 of responding to the spatial signatures.

Stage 950 can include outputting information indicative of a plurality of spatial signatures (stage 951), storing the information (stage 952), transmitting the information (stage 953), displaying the information (stage 954), processing the information and the like.

The information can be displayed as a spatial signature map, wherein similar or identical spatial signatures are represented by the representation. For example, they can be represented by the same color, same symbol, same intensity and the like. Accordingly, a map of the wafer is provided with coded information representative of the spatial signatures that have been found. The spatial signature map can illustrate the shapes of the spatial signatures and also a representation of one or more attributes.

For example, stage 950 can include stage 955 of defining review sites for a review tool in response to detected spatial signatures. The review sites can be diversified between different spatial signatures.

Yet as another example, stage 950 can include stage 956 of triggering a review tool based classification of defects in response to detected spatial signatures. Stage 956 of triggering can occur when the spatial signature process does not provide reliable results.

According to an embodiment of the invention the spatial signatures obtained during stage 930 can assist in finding the best inspection conditions. This can require a repetition of stages 910-950 on wafer defect density maps obtained under different inspection conditions (different defect maps). The inspection conditions (e.g. optical configuration, polarization configuration, sensitivity setting, and one or more defect filtering thresholds including, for example, defect size, defect aspect ratio and signal to noise ratio) can be determined in view of the expected defects to be found. It should be noted that the invention is not limited by the type and kind of the inspection conditions, and many inspection conditions, the adjustment of which would affect the resultant defect map, could be optimized by applying the invention.

Figure 10:
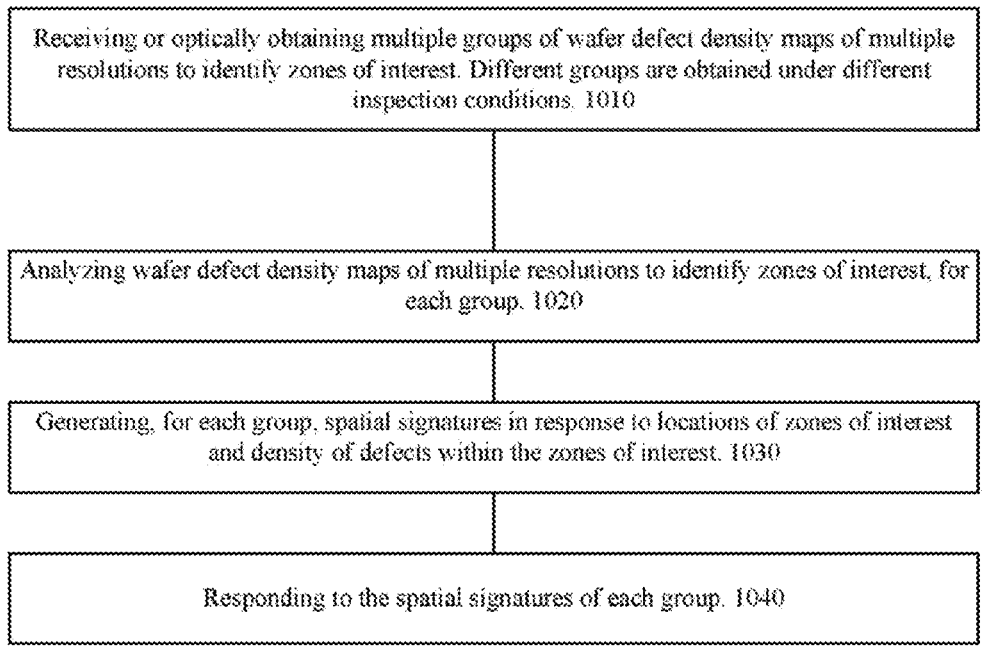
FIG. 10 illustrates an inspection recipe optimization method 1000 according to an embodiment of the invention.

FIG. 10 illustrates a method for operating an inspection tool, e.g. an inspection recipe setup/optimization method 1000 according to an embodiment of the invention.

Method 1000 starts by stage 1010 of receiving or optically obtaining multiple groups of wafer defect density maps of multiple resolutions to identify zones of interest. Different groups are obtained under different inspection conditions (different defect maps).

Stage 1010 is followed by stage 1020 of analyzing wafer defect density maps of multiple resolutions to identify zones of interest, for each group.

Stage 1020 is followed by stage 1030 of generating, for each group, spatial signatures in response to relations between zones of interest and density of defects within the zones of interest.

Stage 1030 is followed by stage 1040 of responding to the spatial signatures of each group.

Stage 1040 can include selecting at least one inspection condition to be applied during an inspection process in response to a comparison between spatial signatures associated with each group. For example, if a certain group detects the highest number of defect signatures, it can include signatures that represents critical defects, and the like.

During the inspection process a very large amount of images of suspected defects can be accumulated. Storing all these images can be impractical, especially if the same inspection tool or process inspects many wafers each day. In order to reduce the storage space required for storing images of suspected defects, a filtering process can be applied and only a small number of the images can be stored. The method illustrated above can assist in determining which images to store.

Referring back to FIG. 9 stage 950 can include stage 953 of selecting images of suspected defects in response to defined spatial signatures. The selected images can be stored while non-selected images of suspected defects are ignored.

According to an embodiment of the invention spatial signatures can be used to tune defect filters of a recipe. The defect filters can filter out insignificant information such as defect information that does not match any spatial signature. A defect map can be generated to include only defects that comply with a valid spatial signature.

According to an embodiment of the invention, a system includes a memory unit for storing wafer defect density maps of multiple resolutions; an analyzer for analyzing the wafer defect density maps to identify zones of interest; a spatial signature generator for generating spatial signatures in response to relations between zones of interest and density of defects within the zones of interest; and a spatial signature response module.

The system can optically obtain one or more images of the wafer and can, additionally or alternatively generate the defect density maps of multiple resolutions, but this is not necessarily so. For example, the system may receive (by memory unit) the wafer defect density maps.

The analyzer can execute stage 910, the spatial signature generator can execute stage 930 and the spatial signature response module can execute stage 950, but this is not necessarily so.

The components of the system can include hardware components, software components or a combination thereof. These components can be located at the same location, integrated with each other, located in different and even remote locations, and the like.

The invention was described mainly with reference to wafer inspection. It should be understood that the invention is not limited to wafer inspection and is applicable, with the required modifications and alterations, to inspect masks, PCBs (Printed Circuit Boards), solar panels or any other substrate for defects.

While certain features of the invention have been illustrated and described herein, many modifications, substitutions, changes, and equivalents will now occur to those of ordinary skill in the art. It is, therefore, to be understood that the appended claims are intended to cover all such modifications and changes which fall within the true spirit of the invention.

Those skilled in the art will readily appreciate that various modifications and changes can be applied to the embodiments of the invention as hereinbefore described without departing from its scope defined in and by the appended claims.

What is claimed is:

1. A method, comprising:
analyzing a plurality of wafer defect density maps to identify one or more zones of interest on each of the plurality of wafer defect density maps, each of the plurality of wafer defect density maps indicating defect densities at a plurality of areas on a wafer and each being at a different resolution associated with a different size of the plurality of areas, the plurality of wafer defect density maps being derived from a single defect map of the wafer obtained by an inspection tool and including information concerning the plurality of areas on the wafer, and the zones of interest representing those areas of the plurality of areas on the wafer containing defects with a density above a predetermined number of defects per area;
generating spatial signatures in response to relations between the zones of interest and the defect densities within the zones of interest; and
performing an inspection process responsive to information obtained from the spatial signatures.

2. The method according to claim 1, wherein the spatial signatures are generated by limiting a defect density variation with each spatial signature.

3. The method according to claim 1, wherein at least two of the zones of interest partially overlap with one another.

4. The method according to claim 1, wherein at least one of the spatial signatures comprises a set of zones of interest; wherein the set comprises a peak zone of interest and at least one other zone of interest; wherein a defect density of the peak zone of interest is higher than a defect density of each of the at least one other zone of interest; and wherein the peak zone of interest is included within another zone of interest of the set.

5. The method according to claim 4, further comprising limiting a defect density variation of the zones of interest of each of the spatial signatures.

6. The method according to claim 4, wherein at least one of the spatial signatures comprises multiple sets of zones of interest.

7. The method according to claim 6, further comprising limiting a defect density variation within the multiple sets of zones of interest.

8. The method according to claim 4, wherein at least one of the spatial signatures comprises multiple sets of zones of interest and wherein each set comprises zones of interest of at least a minimal number of defect density levels.

9. The method according to claim 1, further comprising filtering ones of the spatial signatures that are sparse.

10. The method according to claim 1, further comprising clustering ones of the spatial signatures that resemble each other.

11. A system, comprising:
a memory unit configured to store a plurality of wafer defect density maps, each of the plurality of wafer defect density maps indicating defect densities at a plurality of areas on a wafer and each being at a different resolution associated with a different size of the plurality of areas, the plurality of wafer defect density maps being derived from a single defect map of the wafer obtained by an inspection tool and including information concerning the plurality of areas on the wafer;
an analyzer configured to analyze the plurality of wafer defect density maps to identify one or more zones of interest on each of the plurality of wafer defect density maps, the zones of interest representing those areas of the plurality of areas on the wafer containing defects with a density above a predetermined number of defects per area; and
a spatial signature generator configured to generate spatial signatures in response to relations between the zones of interest and the defect densities within the zones of interest; and
a spatial signature response module configured to select an inspection condition to be applied during an inspection process, the selection being responsive to information obtained from the spatial signatures.

12. The system according to claim 11, wherein the spatial signature response module is configured to define review sites for a review tool in response to the generated spatial signatures.

13. The system according to claim 11, wherein the spatial signature generator is configured to associate multiple attributes to each of the spatial signatures.

14. They system according to claim 11, wherein the spatial signature response module is configured to diversify review sites between the spatial signatures.

15. The system according to claim 11, wherein the spatial signature response module is configured to trigger a review tool based classification of defects in response to the generated spatial signatures.

16. The system according to claim 11, wherein the spatial signature response module is configured to select images of suspected defects in response to the generated spatial signatures.

17. The system according to claim 16, wherein the spatial signature response module is further configured to store the selected images of suspected defects while not storing non-selected images of suspected defects.

* * * * *